(12) United States Patent
Boaz

(10) Patent No.: US 6,210,956 B1
(45) Date of Patent: Apr. 3, 2001

(54) OPTICALLY ACTIVE CIS-1,3-CYCLOHEXANEDICARBOXYLIC ACID MONOESTERS WITH HIGH ENANTIOMERIC PURITY AND PROCESS FOR THEIR PREPARATION

(75) Inventor: Neil W. Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/344,370

(22) Filed: Jun. 25, 1999

Related U.S. Application Data

(62) Division of application No. 09/060,959, filed on Apr. 16, 1998, now Pat. No. 6,028,213.

(51) Int. Cl.$^7$ .............................. C12P 41/00; C07C 1/04
(52) U.S. Cl. ............................................................ 435/280
(58) Field of Search ............................................. 435/280

(56) References Cited

FOREIGN PATENT DOCUMENTS

| 337 348 | 10/1989 | (EP) . |
|---|---|---|
| 92/10099 | 6/1992 | (WO) . |

OTHER PUBLICATIONS

Jones et al., *J. Org. Chem.* 52:4565–4570 (1987).
Gais et al., *Leibing Ann. Chem.* 687–716 (1986).
Lam et al., *J. Am. Chem. Soc.* 110:4409–4411 (1988).
Schneider et al., *Angew. Chem. Int. Ed. Engl.* 23:67–68 (1984).
Turbanti et al., *J. Med. Chem.* 36:699–707 (1993).
Hamilton et al., *J. Org. Chem.* 58:7263–7270 (1993).
Brion et al., *J. Tetrahedron Lett.* 34:4889–4892 (1994).
Borzilleri et al., *J. Am. Chem. Soc.* 116:9789–9790 (1994).
Chenevert et al., *Tetrahedron; Asymmetry.* 3:199–200 (1992).
Chenevert et al., *Chem. Lett.* 93–96 (1994).
Corfield et al., *J. Macromol. Sci. Chem.* A5(1):3 –20 (1971).

*Primary Examiner*—Sandra E. Saucier
(74) *Attorney, Agent, or Firm*—Michael J. Blake; Harry J. Gwinnetl

(57) ABSTRACT

Optically active cis-1,3-cyclohexanedicarboxylic acid monoesters of >90% enantiomeric excess (ee) and methods of preparing the monoesters are described. One method contacts a cis-1,3-cyclohexanedicarboxylic acid diester with a lipase under aqueous conditions to enantioselectively produce the optically active cis-1,3-cyclohexanedicarboxylic acid monoester. Another method reacts a mixture of cis- and trans-1,3-cyclohexanedicarboxylic acids under conditions sufficient to form a cis-cyclic anhydride, esterifies the cis-cyclic anhydride to produce a cis-1,3-cyclohexanedicarboxylic acid diester and then contacts under aqueous conditions the diester with a lipase to enantioselectively produce the optically active cis-1,3-cyclohexanedicarboxylic acid monoester.

16 Claims, No Drawings

OPTICALLY ACTIVE CIS-1,3-CYCLOHEXANEDICARBOXYLIC ACID MONOESTERS WITH HIGH ENANTIOMERIC PURITY AND PROCESS FOR THEIR PREPARATION

This is a divisional of application Ser. No. 09/060,959 filed on Apr. 16, 1998 now U.S. Pat. No. 6,028,213.

BACKGROUND OF THE INVENTION

1. Field of the Invention

The invention relates optically active cis-1,3-cyclohexanedicarboxylic acid monoesters of high enantiomeric purity. The invention also relates a method of preparing optically active cis-1,3-cyclohexanedicarboxylic acid monoesters of high enantiomeric purity. The monoesters may be used as chiral precursors for non-naturally occuring amino acids such as those used to prepare a variety of pharmaceuticals. The monoesters or their derivatives may also be used as chiral polyester modifiers to change the plasticity, melting point, glass transition temperature, chirality or other properties of the polyester.

2. Description of the Related Art

Enzyme-catalyzed hydrolysis reactions are known methods for the generation of asymmetry within a molecule. Oftentimes racemic mixtures of a compound are subjected to enzyme-catalyzed hydrolysis to aid in the resolution of the racemic mixture, i.e. the separation of a racemic mixture into its two optically active components. However, such reactions are often inefficient and at best afford a 50% yield of each enantiomer. In an effort to improve efficiency, enzyme-catalyzed hydrolysis of prochiral meso substrates rather than racemic mixtures has been attempted.

Enantioselective enzyme-catalyzed hydrolysis of cis-1,2-isomers of cyclohexane-dicarboxylic acid diesters has been achieved using the enzyme pig liver esterase. Jones et al., *J. Org. Chem.* 52, 4565 (1987); Gais et al., *Leibings Ann. Chem.* 687 (1986); Lam et al., *J. Am. Chem. Soc.* 110, 4409 (1988); Schneider et al., *Angew. Chem. Int. Ed. Engl.* 23, 67 (1984). The 1,2-isomers have found use in the synthesis of both pharmaceutically active materials and natural products. Turbanti et al., *J. Med. Chem.* 36, 699 (1993); EP 337,348; Hamilton et al., *J. Org. Chem.* 58, 7263 (1993); WO 92 10,099; Brion et al., *J. Tetrahedron Lett.* 34, 4889 (1994); Borzilleri et al., *J. Am. Chem. Soc.* 116, 9789 (1994).

There have also been reports of the desymmetrization of both cis-1,3-cyclopentane-dicarboxylic anhydride via enzymatic alcoholysis and cis-1,3-cyclopentanedicarboxylic acid diesters via enzyme-catalyzed hydrolysis. Chenevert et al., *Tetrahedron; Asymmetry.* 3, 199 (1992); Chenevert et al., *Chem. Lett.* 93 (1994). However, only a single sense of asymmetry, i.e. one enantiomer, was realized in each case. Furthermore, the one enantiomer could only be obtained in ≦91% ee.

In theory, such selective reactions of one of the prochiral groups of the meso substrate would lead to the "desymmetrization" of the meso substrate and theoretically may optimally afford a 100% yield of an optically pure product. This type of process has been termed the "meso trick." Enzyme-catalyzed hydrolysis of a "meso" substrate would also offer the advantage of producing a single species where the reaction of a racemate produced two—an ester of one enantiomer and an alcohol or acid of the other. Thus, an additional separation step is avoided by application of a desymmetrization reaction.

Thus, despite the processes described above, there remains a need in the art for a process for producing optically active cis-1,3-cyclohexanedicarboxylic acid monoesters that offers high enantioselectivity.

SUMMARY OF THE INVENTION

It has now been discovered that by use of a lipase, a cis-1,3-cyclohexanedicarboxylic acid diester may be converted to an optically active cis-1,3-cyclohexanedicarboxylic acid monoester with a high degree of enantioselectivity (>90% ee).

Accordingly, the invention relates a method of preparing an optically active cis-1,3-cyclohexanedicarboxylic acid monoester by contacting under aqueous conditions a substituted or unsubstituted cis-1,3-cyclohexanedicarboxylic acid diester of formula (I):

(I)

with a lipase capable of enantioselectively converting the diester to a substituted or unsubstituted cis-1,3-cyclohexanedicarboxylic acid monoester in >90% enantiomeric excess of either formula (II) or formula (III):

(II)

(III)

The invention also relates a method of preparing an optically active cis-1,3-cyclohexanedicarboxylic acid monoester by reacting a mixture of substituted or unsubstituted cis- and trans-1,3-cyclohexanedicarboxylic acids under conditions sufficient to convert the cis- and trans-1,3-cyclohexanedicarboxylic acids to a substituted or unsubstituted cis-cyclic anhydride, esterifying the cis-cyclic anhydride to produce a substituted or unsubstituted cis-1,3-cyclohexanedicarboxylic acid diester of formula (I):

(I)

and contacting under aqueous conditions the diester of formula (I) with a lipase capable of enantioselectively converting the diester to a substituted or unsubstituted cis-1,3-cyclohexanedicarboxylic acid monoester in >90% enantiomeric excess of formula (II) or formula (III):

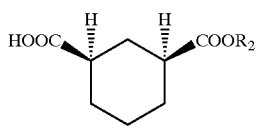

(II)

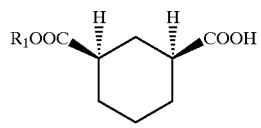

(III)

The invention further relates a composition comprising a substituted or unsubstituted cis-1,3-cyclohexanedicarboxylic acid monoester in >90% enantiomeric excess of either formula (II) or formula (III):

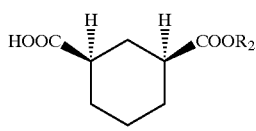

(II)

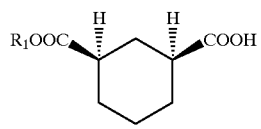

(III)

The invention still further relates a substituted or unsubstituted cis-1,3-cyclohexanedicarboxylic acid monoester of formula (II):

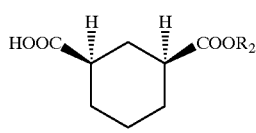

(II)

The invention also relates a substituted or unsubstituted cis-1,3-cyclohexanedicarboxylic acid monoester of formula (III):

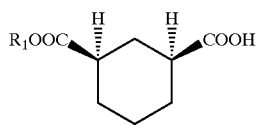

(III)

The invention further relates a racemic composition comprising a substituted or unsubstituted cis-1,3-cyclohexanedicarboxylic acid monoester of formula (II) and formula (III):

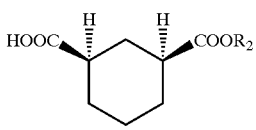

(II)

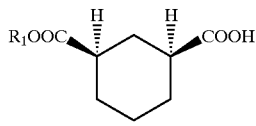

(III)

DETAILED DESCRIPTION OF THE INVENTION

One embodiment of the invention is a method of preparing an optically active substituted or unsubstituted cis-1,3-cyclohexanedicarboxylic acid monoester by contacting under aqueous conditions a substituted or unsubstituted cis-1,3-cyclohexanedicarboxylic acid diester of formula

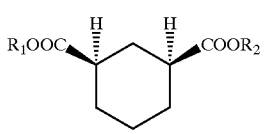

(I)

with a lipase capable of enantioselectively converting the diester to a substituted or unsubstituted cis-1,3-cyclohexanedicarboxylic acid monoester of either formula (II) or formula (III) in >90% enantiomeric excess:

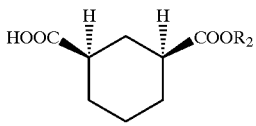

(II)

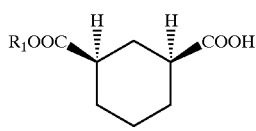

(III)

In formulae (I), (II) and (III), $R_1$ and $R_2$ are, independently, a substituted or unsubstituted, linear or branched $C_2$–$C_{12}$ alkyl group. Preferably, $R_1$ and $R_2$ are the same. In a preferred embodiment, $R_1$ and $R_2$ are the same linear $C_2$–$C_4$ alkyl group, most preferably $R_1$ and $R_2$ are each an ethyl group.

The C4, C5, and C6 positions of the cyclohexane ring of the diester and the cyclohexane ring of the monoester may be substituted with any substituent known in the art such that conversion of the precursor diester to the monoester is not effected. Preferably, the "meso" symmetry of the diester is maintained. Suitable substituents include, but are not limited to, $C_1$–$C_{12}$ alkyl, aryl, heteroaryl, halide (e.g. chloro and bromo), ether, and sulfide groups.

The method of the invention may employ any lipase, commercially available or otherwise, which enantioselectively converts a diester of formula (I) to a substituted or unsubstituted cis-1,3-cyclohexanedicarboxylic acid monoester of formula (II) or formula (III) in >90% enantiomeric excess. The lipase may be used in either a purified or unpurified state. Any amount of purified or unpurified lipase may be used since the reaction generally runs until conversion to the monoester is complete. The time to complete the reaction may depend on the amount of lipase used. The lower the amount of active lipase added, the longer the reaction time. The greater the amount of active lipase added, the shorter the reaction time. Generally, hydrolysis is complete once the monoester of formula (II) or formula (III) forms and enters the aqeuous phase of a biphasic organic/aqueous system, as discussed below, to form a charged species and thus can no longer react with the lipase. Preferably, the purified or unpurified lipase is added such that the weight ratio of the substrate diester of formula (I) to lipase ranges from about 1–1000. In a preferred embodiment, the weight ratio of substrate diester to unpurified lipase ranges from about 1–50, more preferably from about 2–25, most preferably from about 3–11. In a preferred embodiment, the weight ratio of substrate diester to purified lipase ranges from about 100–1000, more preferably from about 125–500, most preferably from about 150–300.

The lipase may be in soluble form or immobilized form as long as enantioselectivity of the hydrolysis is not compromised. Preferably, the lipase is in an immobilized form. Examples of suitable immobilized lipases include, for example, crystallized cross-linked lipases such as ChiroCLEC™ available from Altus Biologics Inc. of Cambridge, Mass. An immobilized lipase offers advantages of being readily removed, for example, by filtration, upon completion of the hydrolysis, to being recyclable for subsequent use, and avoiding potential emulsion problems caused by the presence of a lipase.

Preferably the lipase is selected from a Pseudomonas or Candida species. Examples of suitable enzymes include, but are not limited to, lipase PS-30 from *Pseudomonas cepacia*, lipase AK from Pseudomonas sp., lipase CRL from *Candida rugosa*, lipase AY-30 from *Candida rugosa*, crystallized cross-linked lipase from *Pseudomonas cepacia* (e.g. ChiroCLEC-PC™), crystallized cross-linked lipase from *Candida rugosa* (e.g. ChiroCLEC-CR™), and lipase K10 from Pseudomonas sp. As shown below in the Examples, the lipase used determines whether a cis-1,3-cyclohexanedicarboxylic acid monoester of formula (II) or formula (III) will result from the hydrolysis. In a preferred embodiment of the invention, a cis-1,3-cyclohexanedicarboxylic acid monoester of formula (II) in >90% enantiomeric excess may be prepared by use of a lipase from Pseudomonas sp. such as, for example, lipase PS-30 from *Pseudomonas cepacia*, lipase AK from Pseudomonas sp., crystallized cross-linked lipase from *Pseudomonas cepacia*, and lipase K10 from Pseudomonas sp. In a preferred embodiment of the invention, a cis-1,3-cyclohexanedicarboxylic acid monoester of formula (III) in >90% enantiomeric excess may be prepared by use of a lipase from *Candida rugosa* such as, for example, lipase CRL from *Candida rugosa*, lipase AY-30 from *Candida rugosa*, and crystallized cross-linked lipase from *Candida rugosa*.

By contacting under aqueous conditions the diester of formula (I) with a lipase, one of the ester groups of the diester may be hydrolyzed to a carboxylic acid. In general, a diester of formula (I) is a liquid at room temperature. Thus combining a diester of formula (I) with an aqueous buffer results in a biphasic organic/aqueous system, typically an emulsion. The hydrolysis generally occurs in this biphasic system. Aqueous conditions include the combination of a diester of formula (I) with an aqueous buffer to form a mixture or an emulsion. Any aqueous buffer may be used. Preferably, the aqueous buffer is an aqueous phosphate buffer. An organic co-solvent such as, for example, tetrahydrofuran (THF) may also be added to the substrate/buffer mixture or emulsion.

The conversion of a diester of formula (I) to a monoester of formula (II) or (III) may be conducted at any pH which does not effect lipase activity and which does not promote non-lipase mediated background chemical hydrolysis. Preferably, pH is kept constant at a pH range from about 5 to about 8, most preferably at about pH 7. Constant pH may be maintained using techniques known in the art, including, for example, titration of liberated acid with an aqueous base and/or the presence of an aqueous buffer, such as those aqueous buffers discussed above. The conversion of diester of formula (I) to monoester of formula (II) or (III) may be performed as a biphasic mixture of an organic phase and an aqueous buffered phase.

Generally, conversion of a diester of formula (I) to a monoester of formula (II) or (III) may be conducted at any temperature and pressure as long as lipase activity is not lost. Preferably, the conversion is performed at a temperature range of about 5° C. to about 60° C., more preferably from about 15° C. to about 25° C. In a preferred embodiment, the enzyme-catalyzed hydrolysis is conducted at ambient temperature and pressure.

According to the invention, a substituted or unsubstituted cis-1,3-cyclohexanedicarboxylic acid diester of formula (I), as described above, may be prepared by methods known in the art. Preferably, the diester is prepared by reacting a mixture of substituted or unsubstituted cis- and trans-1,3-cyclohexanedicarboxylic acids of, respectively, formula (IV) and formula (V):

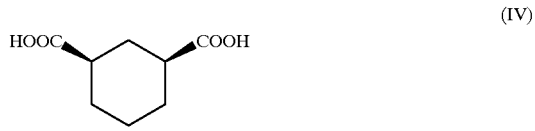

(IV)

(V)

under conditions sufficient to cyclize the cis- and trans-1,3-cyclohexanedicarboxylic acids to the substituted or unsubstituted cis-cyclic anhydride of formula (VI):

(VI)

and esterifying the cis-cyclic anhydride to produce the diester of formula (I). Conditions sufficient to cyclize cis- and trans-1,3-cyclohexanedicarboxylic acids include those known in the art. Examples of such conditions include, but are not limited to, reacting the isomeric mixture of diacids in the presence of an inorganic or organic compound capable of converting the cis- and trans-1,3-cyclohexanedicarboxylic acids to the cis-cyclic anhydride (Corfield et al., *J. Macromol. Sci. Chem.* A5, 3 (1971)). An inorganic or organic compound capable of converting cis- and trans-1,3-cyclohexanedicarboxylic acids to the cis-cyclic anhydride may be any compound known in the art such as, for example, phosphorus pentoxide, phosphorus oxychloride, and acetic anhydride. Preferably, the compound is acetic anhydride. If acetic anhydride is used to produce the cis-cyclic anhydride, distillation of the by-product acetic acid may also be performed to promote conversion to the cis-cyclic anhydride.

If necessary, purification of the resulting cis-cyclic anhydride may be performed using techniques well known in the art such as, for example, distillation, chromatography and recrystallization. Preferably, purification is achieved by recrystallization from, for example, toluene and heptane.

Esterification of the cis-cyclic anhydride may be accomplished using esterification techniques known in the art. Preferably, conversion to the diester of formula (I) is achieved under acid-catalyzed esterification conditions. Preferably, the cis-cyclic anhydride is reacted with at least one alcohol in the presence of an acid catalyst. Selection of alcohol will depend upon the type of diester of formula (I) desired, i.e. the alcohol or alcohols will correspond with $R_1$ and $R_2$ of formula (I). Examples of suitable alcohols include, but are not limited to, ethanol, n-propanol, isopropanol, and n-butanol. In addition, an appropriate orthoformate such as, for example, triethyl orthoformate, which upon reaction with water affords an alcohol and a formate, may also be used. An organic cosolvent such as, for example, toluene, may also be used to promote esterification by facilitating the azeotropic distillation of water. The acid catalyst may be any acid esterification catalyst known in the art. Preferably, the acid catalyst is p-toluenesulfonic acid.

Another embodiment of the invention is a composition comprising a substituted or unsubstituted cis-1,3-cyclohexanedicarboxylic acid monoester in >90% enantiomeric excess of formula (II) or formula (III):

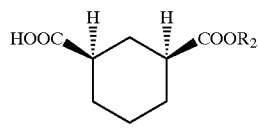

(II)

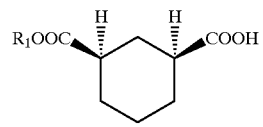

(III)

In formulae (II) and (III), $R_1$ and $R_2$ are each as described above. Likewise the substituent is as described above.

A further embodiment of the invention is a substituted or unsubstituted cis-1,3-cyclohexanedicarboxylic acid monoester of formula (II):

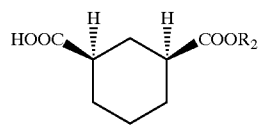

(II)

In formula (II), $R_2$ is as defined above. A monoester of formula (II) may be prepared by any of the methods described above and, if necessary, isolated by techniques known in the art including, for example, recrystallization and chromatography.

A still further embodiment of the invention is a substituted or unsubstituted cis-1,3-cyclohexanedicarboxylic acid monoester of formula (III):

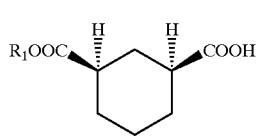

(III)

In formula (III), $R_1$ is as defined above. A monoester of formula (III) may be prepared by any of the methods described above and, if necessary, isolated by techniques known in the art including, for example, recrystallization and chromatography.

Another embodiment of the invention is a racemic composition comprising a substituted or unsubstituted cis-1,3-cyclohexanedicarboxylic acid monoester of formula (II) and formula

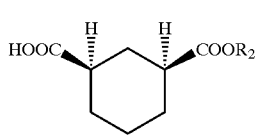

(II)

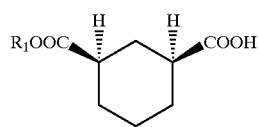

(III)

In formulae (II) and (III), $R_1$ and $R_2$ are a substituted or unsubstituted, linear or branched $C_2$–$C_{12}$ alkyl group. The substituent is as described above.

The following examples are given to illustrate the invention. It should be understood, however, that the invention is not to be limited to the specific conditions or details set forth in these examples.

EXAMPLES

The following examples use the following enzymes not described above:
PS-30, a lipase from *Pseudomonas cepacia*, sold by Amano International Enzyme Co. of Troy, Va.
AK, a lipase from Pseudomonas sp., sold by Amano International Enzyme Co. of Troy, Va. pig liver esterase, sold by Sigma of St. Louis, Mo.
CRL, a lipase from *Candida rugosa*, sold by Sigma of St. Louis, Mo.
AY-30, a lipase from *Candida rugosa*, sold by Amano International Enzyme Co. of Troy, Va.
porcine pancreatic lipase, sold by Aldrich Chemical Co. of Milwaukee, Wis.
D, a lipase from *Rhizopus delemar*, available from Amano International Enzyme Co. of Troy, Va.
AP, a lipase from *Aspergillus niger*, available from Amano International Enzyme Co. of Troy, Va.
ChiroCLEC-PC™, a crystallized cross-linked lipase from *Pseudomonas cepacia*, sold by Altus Biologics Inc. of Cambridge, Mass.
ChiroCLEC-CR™, a crystallized cross-linked lipase from *Candida rugosa*, sold by Altus Biologics Inc. of Cambridge, Mass.

K10, a lipase from Pseudomonas sp., available from Amano International Enzyme Co. of Troy, Va.

MAP-10, a lipase from Mucor sp., available from Amano International Enzyme Co. of Troy, Va.

GC-20, a lipase from *Geotrichum Candidum*, available from Amano International Enzyme Co. of Troy, Va.

L-10, a lipase from Candida sp., available from Amano International Enzyme Co. of Troy, Va.

CES, a lipase from Pseudomonas sp., available from Amano International Enzyme Co. of Troy, Va.

N, a lipase from *Rhizopus niveus*, available from Amano International Enzyme Co. of Troy, Va.

R10, a lipase from *Penicillium roqueforti* available from Amano International Enzyme Co. of Troy, Va.

Example 1
Enantioselectivity of Lipases from Pseudomonas sp. and *Candida rugosa* in the Enzyme-catalyzed hydrolysis of cis-1,3-Cyclohexanedicarboxylic Acid Diester.

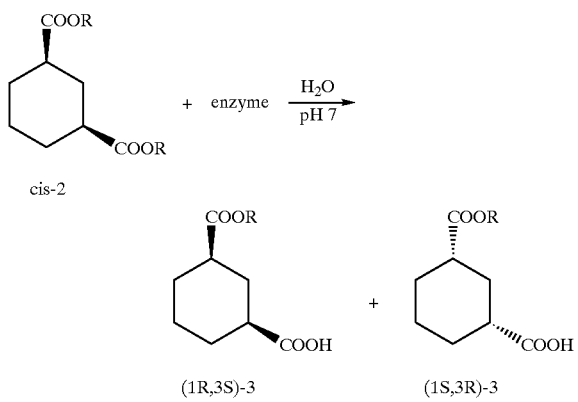

The hydrolysis of various cis-1,3-cyclohexanedicarboxylic acid diesters (cis-2) was screened against the following enzymes: lipase PS-30 from *Pseudomonas cepacia*, lipase AK from Pseudomonas sp., pig liver esterase (PLE), lipase CRL from *Candida rugosa*, and lipase AY-30 from *Candida rugosa*. The results are summarized in Table I.

TABLE I

Enantiomeric Excess* of cis-3 from the Enzyme-catalyzed hydrolysis of cis-2

| R | Enzyme** | | | | |
|---|---|---|---|---|---|
|  | PS-30 | AK | PLE | CRL | AY-30 |
| Me (a) | 82 | 77 | 16 | −98 | −62 |
| Et (b) | 96 | 92 | 34 | −96 | −96 |
| n-Pr (c) | 88 | 88 | 32 | −82 | −95 |
| i-Pr (d) | 54 | 54 | 32 | −99 | −99 |
| n-Bu (e) | 90 | 91 | 47 | −70 | −86 |

*defined as [% (1S,3R)-3]-[% (1R,3S)-3]
**Enzyme key:
PS-30: lipase from *Pseudomonas cepacia* (Amano International Enzyme Co.);
AK: lipase from Pseudomonas sp. (Amano International Enzyme Co.);
PLE: pig liver esterase (Sigma);
CRL: lipase from *Candida rugosa* (Sigma);
AY-30: Lipase from *Candida rugosa* (Amano International Enzyme Co.).

Example 2
Determination of the Absolute Configuration of Cis-1,3-cyclohexanedicarboxylic Acid Monoethyl Esters.

The absolute configuration of the monoethyl ester of cis-1,3-cyclohexanedicarboxylic acid (CHDA) was determined by correlation with commercially available (R)-3-methyl-cyclohexanone (A) through a convergent sequence shown in Scheme I.

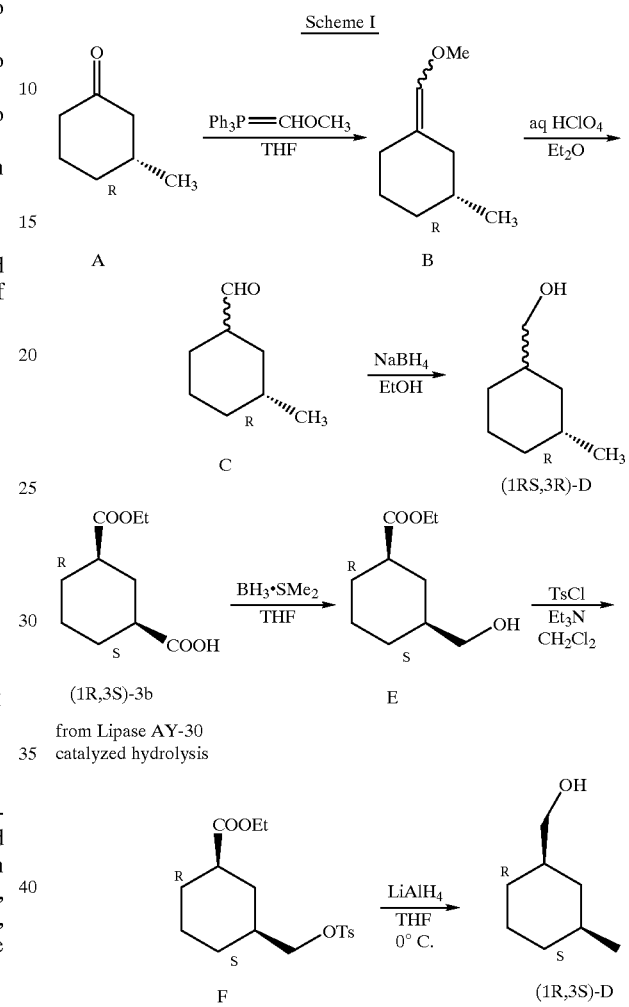

The ketone A was converted to (R)-3-methyl-1-(R,S)-cyclohexanemethanol [(1RS,3R)-D] by a three step sequence entailing Wittig reaction with methoxymethylen-etriphenylphosphorane to afford enol ether B, hydrolysis of the resulting enol ether to the aldehyde C, and reduction of the aldehyde to the alcohol D. Conversely, the monoester derived from Lipase AY-30 hydrolysis was subjected to reduction of the acid moiety to the alcohol E (borane-methyl sulfide), derivatization to the tosylate F, and exhaustive reduction to D. Analysis of the chiral gas chromatography (GC) spectra (30 m Cyclodex-B) of the racemate of D and the two samples prepared above indicated that the material derived from the enzyme-catalyzed hydrolysis was of opposite configuration at the 3-position from the authentic (R)-enantiomer. Thus the absolute configuration of the monoester derived from Lipase AY-30 hydrolysis of diethyl cis-1,3-CHDA was (1R,3S)-1-ethoxycarbonylcyclohexane-3-carboxylic acid and that derived from Lipase PS-30-catalyzed hydrolysis was the (1S,3R)-isomer.

Example 3
Preparation of cis-1,3-Cyclohexanedicarboxylic Anhydride (1):

1,3-Cyclohexanedicarboxylic acid (mixture of cis and trans; 20 g; 0.116 mol) was slurried in acetic anhydride (80 mL; 0.85 mol; 7.3 equiv). The resulting mixture was heated to reflux (at which point it was homogeneous) for 5 h. A distillation head was added and the volatiles were removed by increasing the pot temperature to 200° C. Once no more distillate was collected the residue was cooled to ambient temperature to afford a solid mass. The crude product was recrystallized from hot toluene (40 mL) by the addition of heptane (40 mL) and cooling to 4° C. The precipitated product was filtered, washed with heptane, and dried in vacuo to afford 16.74 g (93%) of 1.

$^1$H NMR (CDCl$_3$) δ 3.063 (br s, 2H); 2.3–2.1 (m, 3H); 1.9–1.3 (m, 5H).

Example 4
Preparation of Dimethyl cis-1,3-Cyclohexanedicarboxylate (cis-2a):

Anhydride 1 (3.85 g; 25 mmol) was combined with trimethyl orthoformate (4.10 mL; 37.5 mmol; 1.5 equiv) and methanol (8.2 mL). p-Toluenesulfonic acid (238 mg; 1.25 mmol; 0.05 equiv) was added and the reaction mixture was stirred overnight at ambient temperature to completely consume 1 and afford a single product by GC analysis. The solvent was removed at reduced pressure and the residue was dissolved in ethyl acetate (30 mL), washed with saturated aqueous NaHCO$_3$ (10 mL), dried over MgSO$_4$, and concentrated to afford 4.91 g (98%) of cis-2a which gave a single peak by GC analysis.

A mixture of cis/trans-2a was prepared from cis/trans-CHDA. Comparison of $^1$H NMR and gas chromatography (GC) data of cis-2a against the data of cis/trans-2a indicated that there was no detectable trans isomer present. The $^1$H NMR and gas chromatography (GC) data for cis-2a and trans-2a are as follows:

cis-2a: $^1$H NMR (CDCl$_3$) δ 3.671 (s, 6 H); 2.3 (m, 3 H); 1.95 m, 3 H); 1.65–1.2 (m, 4H). GC (30 m Cyclodex-B, 175° C. isothermal): t$_R$ 3.64 min.

trans-2a: $^1$H NMR (CDCl$_3$) δ 3.686 (s, 6 H); 2.688 (m. 5), 2 H,J=5.68 Hz). GC (30 m Cyclodex-B, 175° C. isothermal): t$_R$ 3.23 min.

Example 5
Preparation of Diethyl cis-1,3-Cyclohexanedicarboxylate (cis-2b):

Anhydride 1 (7.71 g; 50 mmol) was combined with triethyl orthoformate (12.5 mL; 75 mmol; 1.5 equiv) and ethanol (50 mL). p-Toluenesulfonic acid (0.48 g; 2.5 mmol; 0.05 equiv) was added and the reaction mixture was heated overnight at 60° C. to completely consume 1. Solid sodium bicarbonate (0.5 g) was added and the solvent was removed at reduced pressure. The residue was dissolved in toluene (25 mL), washed with saturated aqueous NaHCO$_3$ (5 mL), dried over Na$_2$SO$_4$, and concentrated to afford 11.42 g (99%) of cis-2b which was a single peak by GC analysis.

A mixture of cis/trans-2b was prepared from cisltrans-CHDA. Comparison of $^1$H NMR and gas chromatography (GC) data of cis-2b against the data of cis/trans-2b indicated that there was no detectable trans isomer present. The $^1$H NMR and gas chromatography (GC) data for cis-2b and trans-2b are as follows:

cis-2b: $^1$H NMR (CDCl$_3$) δ 4.123 (q, 4 H, J=7.14 Hz); 2.4–2.15 (m, 3 H); 2.05–1.85 (m, 3 H); 1.65–1.3 (m, 4H); 1.249 (t, 6H, J=7.14 Hz). GC (30 m Cyclodex-B, 175° C. isothermal): t$_R$ 5.49 min.

trans-2b: $^1$H NMR (CDCl$_3$) δ 4.139 (q, 6 H, J=7.14 Hz); 2.665 (m (5), 2 H, J=5.80 Hz); 1.257 (t, 6H, J=7.26 Hz). GC (30 m Cyclodex-B, 175° C. isothermal): t$_R$ 4.37 min.

Example 6
Preparation of Di-n-propyl cis-1,3-Cyclohexanedicarboxylate (cis-2c):

Anhydride 1 (3.85 g; 25 mmol) was dissolved in toluene (25 mL) and n-propanol (9.3 mL; 125 mmol; 5 equiv). p-Toluenesulfonic acid (238 mg; 1.25 mmol; 0.05 equiv) was added and the reaction mixture was heated to reflux under conditions where water could be continuously distilled using a Dean-Stark trap. After 2 h at reflux, GC analysis indicated no residual 1. The reaction mixture was washed with saturated aqueous sodium bicarbonate (5 mL). The organic solution was dried over MgSO$_4$ and concentrated to afford 6.24 g (97%) of cis-2c which was a single peak by GC analysis.

A mixture of cis/trans-2c was prepared from cis/trans-CHDA. Comparison of $^1$H NMR and gas chromatography (GC) data of cis-2c against the data of cis/trans-2c indicated that there was no detectable trans isomer present. The $^1$H NMR and gas chromatography (GC) data for cis-2c and trans-2c are as follows:

cis-2c: $^1$H NMR (CDCl$_3$) δ 4.0333 (t, 4 H, J=6.72 Hz); 2.4–2.2 (m, 3 H); 2.05–1.85 (m, 3 H); 1.75–1.5 (m, 5H); 1.4–1.25 (m, 3H); 0.940 (t, 6H, J=7.33 Hz). GC (30 m Cyclodex-B, 175° C. isothermal); t$_R$ 9.91 min.

trans-2c: $^1$H NMR (CDCl$_3$) δ 4.044 (t, 4 H, J=6.60 Hz); 2.677 (m (5), 2 H, J=5.74 Hz); 0.946 (t, 6H, J=7.39 Hz). GC (30 m Cyclodex-B, 175° C. isothermal): t$_R$ 8.28 min.

Example 7
Preparation of Di-i-propyl cis-1,3-Cyclohexanedicarboxylate (cis-2d):

Anhydride 1 (1.21 g; 7.8 mmol) was dissolved in isopropanol (6.0 mL; 78 mmol; 10 equiv) and toluene (6 mL). p-Toluenesulfonic acid (74 mg; 0.39 mmol; 0.05 equiv) was added and the reaction mixture was heated to reflux under conditions where water could be continuously distilled using a Dean-Stark trap. After 7 hr at reflux, GC analysis indicated >96% conversion to 2d. The reaction mixture was washed with saturated aqueous sodium bicarbonate (2×10 mL). The organic solution was dried over MgSO$_4$ and concentrated to afford cis-2d which was a single peak by GC analysis.

A mixture of cis/trans-2d was prepared from cis/trans-CHDA. Comparison of $^1$H NMR and gas chromatography (GC) data of cis-2d against the data of cisltrans-2d indicated that there was no detectable trans isomer present. The $^1$H NMR and gas chromatography (GC) data for cis-2d and trans-2d are as follows:

cis-2d: $^1$H NMR (CDCl$_3$) δ 4.997 (m(7), 2 H, J=6.29 Hz); 2.35–2.1 (m, 3 H); 2.0–1.85 (m, 3 H); 1.6–1.3 (m, 4H); 1.222 (d, 12H, J=6.17 Hz). GC (30 m Cyclodex-B, 175° C. isothermal); t$_R$ 5.78 min.

trans-2d: $^1$H NMR (CDCl$_3$) δ 5.010 (m(7) 2 H, J=6.35 Hz); 2.621 (m (5), 2 H, J=5.93 Hz). 1.231 (d, 12H, J=6.16 Hz). GC (30 m Cyclodex-B, 175° C. isothermal): t$_R$ 4.78 min.

Example 8
Preparation of Di-n-butyl cis-1,3-Cyclohexanedicarboxylate (cis-2e):

Anhydride 1 (3.85 g; 25 mmol) was combined with n-butanol (11.4 mL; 125 mmol; 5 equiv) and toluene (25 mL). p-Toluenesulfonic acid (238 mg; 1.25 mmol; 0.05 equiv) was added and the reaction mixture was heated to reflux under conditions where water could be continuously distilled using a Dean-Stark trap. After 2.5 h at reflux, GC analysis indicated no residual 1. The reaction mixture was washed with saturated aqueous sodium bicarbonate (5 mL). The organic solution was dried over $MgSO_4$ and concentrated to afford cis-2e (7.11 g; 99%) which was a single peak by GC analysis.

cis-2e: $^1$H NMR ($CDCl_3$) δ 4.070 (t, 4H, J=6.59 Hz); 2.4–2.15 (m, 3 H); 2.05–1.85 (m, 3 H); 1.7–1.2 (m, 12H); 0.930 (t, 6H, J=7.26 Hz). GC (30 m Cyclodex-B, 175° C. isothermal); $t_R$ 20.49 min.

Example 9
Screening for Enzyme Activity and Selectivity Using Diethyl cis-1,3-Cyclohexanedicarboxylate (2b):

Approximately 20 mg of cis-2b was combined with 1 mL of pH 7 buffer in a 2 mL plastic centrifuge vial. The enzyme (ca. 10 mg) was added and the vial was shaken for 1 day. 3 N HCl (200 μL) was added followed by ethyl acetate (500 μL). The upper organic layer was analyzed by chiral GC to estimate conversion and enantiomer ratio (30 m Cyclodex-B, 175° C., 15 min).

| Enzyme | Conversion | Enantiomer Ratio of 3b (1S,3R):(1R,3S) | % ee**** |
|---|---|---|---|
| PS-30 | 98% | 98:2 | 96 |
| PPL* | 3% | 83:17 | 66 |
| PLE | 54% | 67:33 | 34 |
| CRL | >99% | 2:98 | -96 |
| D** | 30% | 24:76 | -52 |
| AP*** | 20% | 11:89 | -78 |

*Porcine pancreatic lipase (Aldrich Chemical Co.)
**Lipase D from *Rhizopus delemar* (Amano International Enzyme Co.)
***Lipase AP from *Aspergillus niger* (Amano International Enzyme Co.)
****% ee = [%(1S,3R)-3] – [%(1R,3S)-3]

Example 10
Preparation of (1S,3R)-1-Ethoxycarbonylcyclohexane-3-carboxylic acid [(1S,3R)-3b] through Enzyme-catalyzed hydrolysis of Diethyl cis-1,3-Cyclohexanedicarboxylate using Lipase PS-30:

Diethyl cis-1,3-cyclohexanedicarboxylate (1.14 g; 5 mmol) was combined with pH 7 aqueous phosphate buffer (20 g) and the pH was adjusted to 7.0. Lipase PS-30 from *Pseudomonas cepacia* (Amano International Enzyme Co.) (200 mg) was added and the hydrolysis commenced. The reaction was conducted at constant pH 7 by the automatic addition of 1 N NaOH to titrate the liberated acid. After 48 h the uptake of base had halted and the reaction was stopped. Celite (200 mg) was added and the mixture was stirred thoroughly. It was then filtered and the precipitate was washed with water and ethyl acetate. The layers were separated and the aqueous layer was acidified to pH 1 with 3 N HCl. This was extracted with ethyl acetate (3×15 mL), the combined extracts were dried over $MgSO_4$, and the solvent was removed to afford 0.91 g (91%) of (1S,3R)-3b. Examination of this material by chiral capillary GC (30 m Cyclodex-B, 175° C.) indicated 96% ee.

(1S,3R)-3b: $^1$H NMR ($CDC_3$) δ 4.131 (q, 2H, J=7.15 Hz); 2.45–2.2 (m, 3 H); 2.1–1.85 (m, 3 H); 1.568 (q, 1H); J=12.33 Hz); 1.5–1.3 (m, 3H); 1.253 (t, 3H, J=7.14 Hz). GC (30 m Cyclodex-B, 175° C. isothermal); $t_R$ 10.8 min. $[\alpha]_D^{24}$ –2.6° (c 1.15, methanol)

Example 11
Preparation of (1S,3 R)-1-Ethoxycarbonylcyclohexane-3-carboxylic acid [(1S,3R)-3b] through Enzyme-catalyzed hydrolysis of Diethyl cis-1,3-cyclohexanedicarboxylate using ChiroCLEC-PC™:

Diethyl cis-1,3-cyclohexanedicarboxylate (2.28 g; 10 mmol) was combined with pH 7 aqueous phosphate buffer (20 g) and the pH was adjusted to 7. ChiroCLEC-PC™ (Altus Biologics Inc.) (9% aqueous suspension; 89 μL; 8 mg dry weight) was added and the hydrolysis commenced. The reaction was conducted at constant pH 7 by the automatic addition of 1 N NaOH to titrate the liberated acid. After 24 h the uptake of base had halted and the reaction was stopped. The reaction mixture was then filtered to remove the enzyme and the precipitate was washed with ethyl acetate. The pH was adjusted to 1 by the addition of 3 N HCl (5 mL). The layers were allowed to separate (no emulsion) and the bottom aqueous layer was decanted and discarded. The top organic layer was dried over $MgSO_4$ and the solvent was removed to afford 1.98 g (99%) of (1S,3R)-3b. Examination of this material by chiral capillary GC (30 m Cyclodex-B, 175° C.) indicated 94% ee.

Example 12
Preparation of (1R,3S)-1-Ethoxycarbonylcyclohexane-3-carboxylic acid [(1R,3S)-3b] through Enzyme-catalyzed hydrolysis of Diethyl cis-1,3-Cyclohexanedicarboxylate using Lipase AY-30:

Diethyl cis-1,3-cyclohexanedicarboxylate (11.4 g; 50 mmol) was combined with pH 7 aqueous phosphate buffer (50 g) and the pH was adjusted to 7. Lipase AY-30 from *Candida rugosa* (Amano International Enzyme Co.) (1 g) was added and the hydrolysis commenced. The reaction was conducted at constant pH 7 by the automatic addition of 1 N NaOH to titrate the liberated acid. After 25 h the uptake of base had halted. The pH of the mixture was adjusted to <2 by the addition of 3 N HCl (20 mL) and ethyl acetate (50 mL) was added. Celite (5.7 g) was added and the mixture was stirred thoroughly. It was then filtered through a small pad of celite and the precipitate was washed with ethyl acetate. The layers were separated and the aqueous layer was extracted with additional ethyl acetate. The combined extracts were dried over $MgSO_4$ and the solvent was removed to afford 9.04 g (90%) of (1R,3S)-3b. Examination of this material by chiral capillary GC (30 m Cyclodex-B, 175° C.) indicated >96% ee.

(1R,3S)-3b: GC (30 m Cyclodex-B, 175° C. isothermal): $t_R$ 10.5 min. $[\alpha]_D^{24}$+4.0° (c 1.49, methanol)

Example 13
Preparation of (1R,3S)-1-Ethoxycarbonylcyclohexane-3-carboxylic acid [(1R,3S)-3b] through Enzyme-catalyzed hydrolysis of Diethyl cis-1,3-Cyclohexanedicarboxylate using ChiroCLEC-CR™

Diethyl cis-1,3-cyclohexanedicarboxylate (2.28 g; 10 mmol) was combined with pH 7 aqueous phosphate buffer (20 g) and the pH was adjusted to 7.0. ChiroCLEC-CR™ (Altus Biologics Inc.) (6.7% aqueous suspension; 225 μL; 15 mg dry weight) was added and the hydrolysis commenced. The reaction was conducted at constant pH 7.0 by the automatic addition of 1 N NaOH to titrate the liberated acid. After 10 h the uptake of base had halted and the reaction was stopped. The reaction mixture was then filtered to remove the enzyme and the precipitate was washed with water and ethyl acetate. The pH was adjusted to 1 by the addition of 3 N HCl (5 mL). The layers were allowed to separate (no emulsion) and the bottom aqueous layer was extracted with additional ethyl acetate (1.5 mL). The combined organic layer was dried over $MgSO_4$ and the solvent was removed to afford 2.00 g (99%) of (1R,3S)-3b. Examination of this material by chiral capillary GC (30 m Cyclodex-B, 175° C.) indicated >95% ee.

Example 14
Screening for Enzyme Activity and Selectivity using Di-n-propyl cis-1,3-Cyclohexanedicarboxylate (cis-2c)

Approximately 20 mg of cis-2c was combined with 1 mL of pH 7 buffer in a 2 mL plastic centrifuge vial. The enzyme (ca. 10 mg) was added and the vial was shaken for 1 day. 3 N HCl (200 μL) was added followed by ethyl acetate (500 μL). The upper organic layer was analyzed by chiral GC to estimate conversion and enantiomer ratio (30 m Cyclodex-B, 175° C., 15 min).

| Enzyme | Conversion | Enantiomer Ratio of 3c (1S,3R.):(1R,3S) | % ee** |
|---|---|---|---|
| PS-30 | 73% | 96:4 | 92 |
| AK | 28% | 94:6 | 88 |
| K10* | 61% | 96:4 | 92 |
| CRL | 76% | 9:91 | −82 |
| AY-30 | 76% | 3:97 | −94 |

*Lipase K10 from *Pseudomdnas sp.* (Amano International Enzyme Co.)
**% ee = [%(1S,3R)-3] − [%(1R,3S)3]

Example 15
Preparation of (1S,3R)-1-n-Propoxycarbonylcyclohexane-3-carboxylic acid [(1S,3R)-3c] through Enzyme-catalyzed hydrolysis of Di-n-propyl cis-1,3-Cyclohexane- dicarboxylate using Lipase PS-30

Di-n-propyl cis-1,3-cyclohexanedicarboxylate (641 mg; 2.5 mmol) was combined with pH 7 aqueous phosphate buffer (20 g) and the pH was adjusted to 7.0. Lipase PS-30 from *Pseudomonas cepacia* (Amano International Enzyme Co.) (200 mg) was added and the hydrolysis commenced. The reaction was conducted at constant pH 7.0 by the automatic addition of 1 N NaOH to titrate the liberated acid. After 24 h the uptake of base had halted and the reaction was stopped. The mixture was acidified to pH 1 with 3 N HCl, filtered, and the precipitate was washed with water. The filtrate was extracted with ethyl acetate (3×15 mL) and the combined extracts were washed with brine (10 mL), dried over MgSO$_4$, and concentrated to afford 0.84 g (84%) of (1S,3R)-3c. Examination of this material by chiral capillary GC (30 m Cyclodex-B, 175° C.) indicated 94% ee.

(1S,3R)-3e: $^1$H NMR (CDCl$_3$) δ 4.038 (t, 2H, J=6.66 Hz); 2.4–2.2 (m, 3 H); 2.1–1.85 (m, 3 H); 1.7–1.5 (m, 3H); 1.5–1.3 (m, 3H); 0.944 (t, 3H, J=7.45 Hz). GC (30 m Cyclodex-B, 175° C. isothermal): t$_R$ 15.8 min. [α]$_D^{24}$ −3.1° (c 1.34, methanol).

Example 16
Preparation of (1R,3S)-1-n-Propoxycarbonylcyclohexane-3-carboxylic acid [(1R,3S)-3c] through Enzyme-catalyzed hydrolysis of Di-n-propyl cis-1,3-Cyclohexanedicarboxylate using Lipase AY-30

Di-n-propyl cis-1,3-cyclohexanedicarboxylate (641 mg; 2.5 mmol) was combined with pH 7 aqueous phosphate buffer (25 g) and the pH was adjusted to 7.0. Lipase AY-30 from *Candida rugosa* (Amano International Enzyme Co.) (100 mg) was added and the hydrolysis commenced. The reaction was conducted at constant pH 7.0 by the automatic addition of 1 N NaOH to titrate the liberated acid. After 5 h the uptake of base had halted. The pH of the mixture was adjusted to 1 by the addition of 3 N HCl and the mixture was extracted with ethyl acetate (3×5 mL) during which time significant amounts of gel were formed. The combined extracts were washed with brine (10 mL) to remove much of the gel, dried over MgSO$_4$, and the solvent was removed to afford 0.53 g (99%) of (1R,3S)-3c. Examination of this material by chiral capillary GC (30 m Cyclodex-B, 175° C.) indicated 98% ee.

(1R,3S)-3c: GC (30 m Cyclodex-B, 175° C. isothermal): t$_R$ 14.8 min. [α]$_D^{24}$+3.9° (c, 1.49, methanol).

Example 17
Screening for Enzyme Activity and Selectivity using Di-i-propyl cis-1,3-Cyclohexanedicarboxylate (cis-2d)

Approximately 20 mg of cis-2d was combined with 1 mL of pH 7 buffer in a 2-mL plastic centrifuge vial. The enzyme (ca. 10 mg) was added and the vial was shaken for 18 h. 3 N HCl (200 μL) was added followed by ethyl acetate (500 μL). The upper organic layer was analyzed by chiral GC to estimate conversion and enantiomer ratio (30 m Cyclodex-B, 175° C., 15 min).

| Enzyme | Conversion | Enantiomer Ratio of d. (3R,1S):(3S,1R) | % ee*** |
|---|---|---|---|
| PS-30 | 6% | 77:23 | 54 |
| AK | 6% | 76:24 | 52 |
| K10 | 3% | 76:24 | 52 |
| AY-30 | 92% | 1:99 | −98 |
| PPL | 1% | 39:61 | −22 |
| PLE | * | * | * |
| D | 9% | 52:48 | 4 |
| MAP-10** | 4% | 54:46 | 8 |
| GC-20** | 10% | 58:42 | 16 |
| L-10** | 7% | 57:43 | 14 |
| CES** | 15% | 69:31 | 38 |
| N** | 7% | 54:46 | 8 |
| R10** | 5% | 50:50 | 0 |

*cis/trans isomerization noted as well as non-selective hydrolysis
**Enzyme key:
MAP-10: Lipase MAP-10 from *Mucor sp.* (Amano International Enzyme Co.);
GC-20: Lipase GC-20 from *Geotrichum Candidum* (Amano International Enzyme Co.);
L-10: Lipase L-10 from *Candida sp.* (Amano International Enzyme Co.);
CES: Lipase CES from *Pseudomonas sp.* (Amano International Enzyme Co.);
N: Lipase N from *Rhizopus niveus* (Amano International Enzyme Co.);
R10: Lipase R10 form *Penicillium roqueforti* (Amano International Enzyme Co.)
***% ee = [%(1R,3S)-3] − [%(1R,3S)-3]

Example 18
Preparation of (1R,3S)-1-i-Propoxycarbonylcyclohexane-3-carboxylic acid [(1R,3S)-d.] through Enzyme-catalyzed hydrolysis of Di-i-propyl cis-1,3-Cyclohexane dicarboxylate using Lipase AY-30

Di-i-propyl cis-1,3-cyclohexanedicarboxylate (641 mg; 2.5 mmol) was combined with pH 7 aqueous phosphate buffer (20 g) and the pH was adjusted to 7. Lipase AY-30 from *Candida rugosa* (Amano International Enzyme Co.) (100 mg) was added and the hydrolysis commenced. The reaction was conducted at constant pH 7 by the automatic addition of 1 N NaOH to titrate the liberated acid. After 14 h the uptake of base had halted. The pH of the mixture was adjusted to 1 by the addition of 3 N HCl and the mixture was extracted with ethyl acetate (3×15 mL) during which time significant amounts of gel were formed. The combined extracts were washed with brine (10 mL) to remove the gel, dried over MgSO$_4$, and the solvent was removed to afford 0.51 g (95%) of (1R,3S)-d. Examination of this material by chiral capillary GC (30 m Cyclodex-B, 175° C.) indicated >98% ee.

(1R,3S)-d.: $^1$H NMR (CDCl$_3$) δ 5.001 (m(7), 1H, J=6.29 Hz); 2.4–2.2 (m, 3H); 2.1–1.85 (m, 3H); 1.7–1.5 (m, 3H) 1.553 (q, 1H, J=12.46 Hz); 1.45–1.3 (m, 3H); 1.224 (d, 6H,

J=6.23 Hz). GC (30 m Cyclodex-B, 165° C. isothermal): $t_R$ 16.4 min. $[\alpha]_D^{24}$+4.7° (c 1.525, methanol)

Example 19

Screening for Enzyme Activity and Selectivity using Di-n-butyl cis-1,3-Cyclohexanedicarboxylate (cis-2e)

Approximately 20 mg of cis-2e was combined with 1 mL of pH 7 buffer in a 2 mL plastic centrifuge vial. The enzyme (ca. 20 mg) was added and the vial was shaken for 1 day. 3 N HCl (200 µL) was added followed by ethyl acetate (500 µL). The upper organic layer was analyzed by chiral GC to estimate conversion and enantiomer ratio (30 m Cyclodex-B, 175° C.).

| Enzyme | Conversion | Enantiomer Ratio of 3e (1S,3R):(1R,3S) | % ee* |
|---|---|---|---|
| PS-30 | 36% | 95:5 | 90 |
| AK | 16% | 95:5 | 90 |
| K10 | 41% | 95:5 | 90 |
| CRL | 25% | 15:85 | −70 |
| AY-30 | 31% | 7:93 | −86 |
| PLE | 3% | 73:27 | 46 |
| PPL | 4% | 49:51 | −2 |

*% ee = [%(1S,3R)-3] − [%(1R,3S)-3]

Example 20

Preparation of (1R,3S)-1-n-Butoxycarbonylcyclohexane-3-carboxylic acid [(1R,3S)-3e] through Enzyme-catalyzed hydrolysis of Di-n-butyl cis-1,3-Cyclohexanedicarboxylate using Lipase AY-30

Di-n-butyl cis-1,3-cyclohexanedicarboxylate (711 mg; 2.5 mmol) was combined with pH 7 aqueous phosphate buffer (20 g) and the pH was adjusted to 7.0. Lipase AY-30 from *Candida rugosa* (Amano International Enzyme Co.) (100 mg) was added and the hydrolysis commenced. The reaction was conducted at constant pH 7 by the automatic addition of 1 N NaOH to titrate the liberated acid. After 16 h the uptake of base had halted. The pH of the mixture was adjusted to 1 by the addition of 3 N HCl and the mixture was extracted with ethyl acetate (3×15 mL) during which time significant amounts of gel were formed. The combined extracts were washed with brine (10 mL) to remove most of the gel, dried over MgSO$_4$, and the solvent was removed to afford 0.54 g (95%) of (1R,3S)-3e:

(1R,3S)-3e: $^1$H NMR (CDCl$_3$) δ 4.077 (t, 2H, J=6.60 Hz); 2.5–2.2 (m, 3 H); 2.1–1.85 (m, 3 H); 1.7–1.5 (m, 3H); 1.5–1.3 (m, 5H); 0.935 (t, 3H, J=7.26 Hz). GC (30 m Cyclodex-B, 165° C. isothermal): $t_R$ 21.6 min. $[\alpha]_D^{24}$−3.1° (c 1.525, methanol)

Comparative Example 1

Screening for Enzyme Activity and Selectivity using Dimethyl cis-1,3-Cyclohexanedicarboxylate (cis-2a)

Approximately 20 mg of cis-2a was combined with 0.75 mL of pH 7 buffer in a 2 mL plastic centrifugal vial. The enzyme (ca. 10 mg) was added and the vial was shaken for 1 day. 3 N HCl (200 µL) was added followed by ethyl acetate (500 µL). The upper organic layer was analyzed by chiral GC to estimate conversion and enantiomer ratio (30 m Cyclodex-B, 175° C., 15 min).

| Enzyme | Conversion | Enantiomer Ratio of 3a (1S,3R):(1R,3S) | % ee* |
|---|---|---|---|
| PS-30 | 87% | 91:9 | 82 |
| PPL | 17% | 68:32 | 36 |
| PLE | 48% | 58:42 | 16 |
| CRL | 98% | 1:99 | −98 |
| D | 3% | 49:51 | −2 |
| AP | 11% | 58:42 | 16 |

*% ee = [%(1S,3R)-3] − [%(1R,3S)-3]

Comparative Example 2

Preparation of (1R,3S)-1-Methoxycarbonylcyclohexane-3-carboxylic acid [(1R,3S)-3a] through Enzyme-catalyzed hydrolysis of Dimethyl cis-1,3-Cyclohexanedicarboxylate using Lipase AY-30

Dimethyl cis-1,3-cyclohexanedicarboxylate (1.0 g; 5 mmol) was combined with pH 7 aqueous phosphate buffer (20 g) and the pH was adjusted to 7.0. Lipase AY-30 from *Candida rugosa* (Amano International Enzyme Co.) (100 mg) was added and the hydrolysis commenced. The reaction was condensed at constant pH 7 by the automatic addition of 1 N NaOH to titrate the liberated acid. After 22 h the uptake of base had halted. The pH of the mixture was adjusted to 1 by the addition of 3 N HCl and the mixture was extracted with ethyl acetate (3×20 mL) during which time significant amounts of gel were formed. The combined extracts were dried over Na$_2$SO$_4$, and the solvent was removed to afford 0.81 g (87%) of (1R,3S)-3a. Examination of this material by chiral capillary GC (30 m Cyclodex-B, 165° C.) indicated 62% ee.

(1R,3S)-3a: $^1$H NMR (CDCl$_3$) δ 3.675 (2,3 H) 2.4–2.2 (m, 3H); 2.1–1.85 (m, 3 H); 1.564 (q, 1 H, J=12.57 Hz); 1.5–1.3 (m, 3 H). GC (30 m Cyclodex-B, 165° C. isothermal): $t_R$ 12.4 min. $[\alpha]_D^{24}$+0.7° (c 1.12, methanol).

The claimed invention is:

1. A method of preparing an optically active cis-1,3-cyclohexanedicarboxylic acid monoester comprising the step of:

contacting under aqueous conditions a substituted or unsubstituted cis-1,3-cyclohexanedicarboxylic acid diester of formula (I):

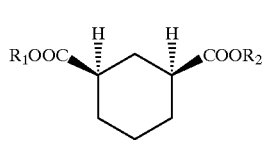

(I)

where R$_1$ and R$_2$ are, independently, a substituted or unsubstituted, linear or branched C$_2$–C$_{12}$ alkyl group, with a lipase capable of enantioselectively converting said diester to a substituted or unsubstituted cis-1,3-cyclohexanedicarboxylic acid monoester in >90% enantiomeric excess of formula (II) or formula (III):

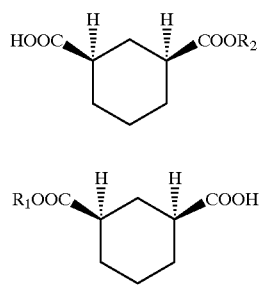

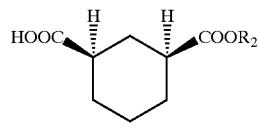

where $R_1$ and $R_2$ are, independently, a substituted or unsubstituted, linear or branched $C_2$–$C_{12}$ alkyl group.

2. A method according to claim 1, wherein said lipase is from a Pseudomonas or a Candida species.

3. A method according to claim 2, wherein said lipase is selected from the group consisting of lipase PS-30 from *Pseudomonas cepacia*, lipase AK from Pseudomonas sp., lipase CRL from *Candida rugosa*, lipase AY-30 from *Candida rugosa*, crystallized cross-linked lipase from *Pseudomonas cepacia*, crystallized cross-linked lipase from *Candida rugosa*, and lipase K10 from Pseudomonas sp.

4. A method according to claim 3, wherein said cis-1,3-cyclohexanedicarboxylic acid monoester is of formula (II):

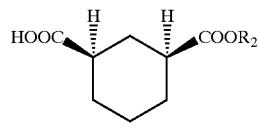

and said lipase is selected from the group consisting of lipase PS-30 from *Pseudomonas cepacia*, lipase AK from Pseudomonas sp., crystallized cross-linked lipase from *Pseudomonas cepacia*, and lipase K10 from Pseudomonas sp.

5. A method according to claim 3, wherein said cis-1,3-cyclohexanedicarboxylic acid monoester is of formula (III):

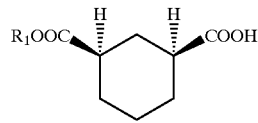

and said lipase is selected from the group consisting of lipase CRL from *Candida rugosa*, lipase AY-30 from *Candida rugosa*, and crystallized cross-linked lipase from *Candida rugosa*.

6. A method according to claim 1, wherein $R_1$ and $R_2$ are the same.

7. A method according to claim 6, wherein $R_1$ and $R_2$ are a linear $C_2$–$C_4$ alkyl group.

8. A method according to claim 7, wherein $R_1$ and $R_2$ are each an ethyl group.

9. A method of preparing an optically active cis-1,3-cyclohexanedicarboxylic acid monoester comprising the steps of:

reacting a mixture of substituted or unsubstituted cis- and trans-1,3-cyclohexanedicarboxylic acids of formulae (IV) and (V):

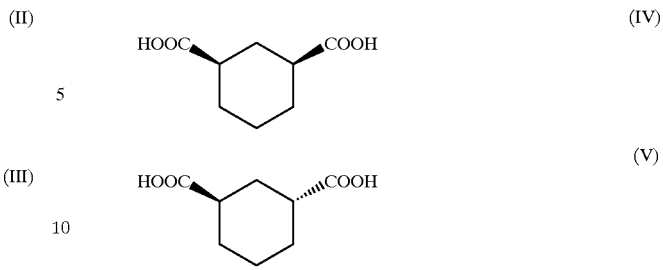

under conditions sufficient to convert said mixture to a substituted or unsubstituted cis-cyclic anhydride of formula (VI):

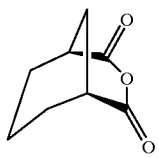

esterifying said cis-cyclic anhydride to produce a substituted or unsubstituted cis-1,3-cyclohexanedicarboxylic acid diester of formula (I):

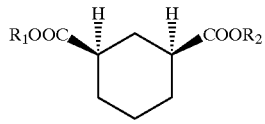

where $R_1$ and $R_2$ are, independently, a substituted or unsubstituted, linear or branched $C_2$–$C_{12}$ alkyl group; and contacting under aqueous conditions said cis-1,3-cyclohexanedicarboxylic acid diester of formula (I) with a lipase capable of enantioselectively converting said diester to a substituted or unsubstituted cis-1,3-cyclohexanedicarboxylic acid monoester in >90% enantiomeric excess of formula (II) or formula (III):

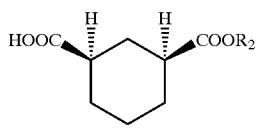

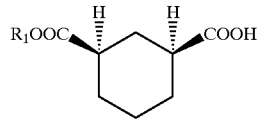

where $R_1$ and $R_2$ are, independently, a substituted or unsubstituted, linear or branched $C_2$–$C_{12}$ alkyl group.

10. A method of claim 9, wherein said lipase is from a Pseudomonas or a Candida species.

11. A method according to claim 10, wherein said lipase is selected from the group consisting of lipase PS-30 from

*Pseudomonas cepacia*, lipase AK from Pseudomonas sp., lipase CRL from *Candida rugosa*, lipase AY-30 from *Candida rugosa*, crystallized cross-linked lipase from *Pseudomonas cepacia*, crystallized cross-linked lipase from *Candida rugosa*, and lipase K10 from Pseudomonas sp.

12. A method according to claim 11, wherein said cis-1,3-cyclohexanedicarboxylic acid monoester is of formula (II):

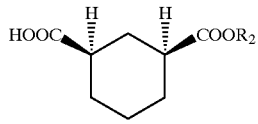

and said lipase is selected from the group consisting of lipase PS-30 from *Pseudomonas cepacia*, lipase AK from Pseudomonas sp., crystallized cross-linked lipase from *Pseudomonas cepacia*, and lipase K10 from Pseudomonas sp.

13. A method according to claim 11, wherein said cis-1,3-cyclohexanedicarboxylic acid monoester is of formula (III):

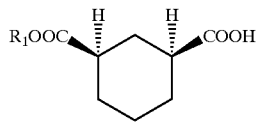

and said lipase is selected from the group consisting of lipase CRL from *Candida rugosa*, lipase AY-30 from *Candida rugosa*, and crystallized cross-linked lipase from *Candida rugosa*.

14. A method according to claim 11, wherein $R_1$ and $R_2$ are the same.

15. A method according to claim 14, wherein $R_1$ and $R_2$ are a linear $C_2$–$C_4$ alkyl group.

16. A method according to claim 15, wherein $R_1$ and $R_2$ are each an ethyl group.

* * * * *